US010980933B2

(12) United States Patent
Prendergast et al.

(10) Patent No.: US 10,980,933 B2
(45) Date of Patent: Apr. 20, 2021

(54) SYSTEM AND METHOD FOR PLATELET REMOVAL DURING MONONUCLEAR CELL COLLECTION

(71) Applicant: Fenwal, Inc., Lake Zurich, IL (US)

(72) Inventors: Jonathan W. Prendergast, Palatine, IL (US); Lan T. Nguyen, Vernon Hills, IL (US); Katherine N. Radwanski, Highland Park, IL (US)

(73) Assignee: Fenwal, Inc., Lake Zurich, IL (US)

( * ) Notice: Subject to any disclaimer, the term of this patent is extended or adjusted under 35 U.S.C. 154(b) by 186 days.

(21) Appl. No.: 16/435,777

(22) Filed: Jun. 10, 2019

(65) Prior Publication Data

US 2019/0290832 A1 Sep. 26, 2019

Related U.S. Application Data

(62) Division of application No. 15/693,799, filed on Sep. 1, 2017, now Pat. No. 10,363,355.

(60) Provisional application No. 62/397,434, filed on Sep. 21, 2016.

(51) Int. Cl.
*A61M 1/36* (2006.01)
*A61M 1/38* (2006.01)
*B01D 63/16* (2006.01)
*A61M 1/34* (2006.01)
*A61M 1/02* (2006.01)

(52) U.S. Cl.
CPC ........ *A61M 1/3693* (2013.01); *A61M 1/0209* (2013.01); *A61M 1/3496* (2013.01); *A61M 1/361* (2014.02); *A61M 1/38* (2013.01); *A61M 1/382* (2013.01); *A61M 1/385* (2013.01); *B01D 63/16* (2013.01); *A61M 1/3672* (2013.01); *A61M 2202/0427* (2013.01); *A61M 2202/0439* (2013.01); *A61M 2202/0443* (2013.01)

(58) Field of Classification Search
CPC ...... A61M 1/3693; A61M 1/38; A61M 1/382; A61M 1/361; A61M 1/0209; A61M 1/385; A61M 1/3496; A61M 1/3672; A61M 2202/0439; A61M 2202/0427; A61M 2202/0443; B01D 63/16
See application file for complete search history.

(56) References Cited

U.S. PATENT DOCUMENTS 5,360,542 A 11/1994 Williamson, IV et al.
6,027,657 A 2/2000 Min et al.

FOREIGN PATENT DOCUMENTS

| EP | 3189865 A2 | 7/2017 |
| WO | 91/18675 A1 | 12/1991 |
| WO | 99/01197 A1 | 1/1999 |
| WO | 2012125457 A1 | 9/2012 |

OTHER PUBLICATIONS

Extended European Search Report for EP Application No. 17190364.4, dated Feb. 6, 2018, 7 pages.

*Primary Examiner* — John Kim
(74) *Attorney, Agent, or Firm* — Cook Alex Ltd.

(57) ABSTRACT

A method of collecting mononuclear cells, comprising separating whole blood into cellular components and platelets suspended in plasma, separating the platelets suspended in plasma into platelet concentrate and platelet-poor plasma, combining the cellular components with the platelet-poor plasma to form a first mixture, and separating the first mixture into mononuclear cells and at least one component.

20 Claims, 7 Drawing Sheets

SYSTEM AND METHOD FOR PLATELET REMOVAL DURING MONONUCLEAR CELL COLLECTION

This application is a divisional of U.S. patent application Ser. No. 15/693,799, filed Sep. 1, 2017, which claims the benefit of U.S. Provisional Patent App. No. 62/397,434 filed Sep. 21, 2016, each of which is expressly incorporated herein by reference in its entirety.

CROSS-REFERENCE TO RELATED APPLICATIONS

This application claims the benefit of U.S. Provisional Patent App. No. 62/397,434 filed Sep. 21, 2016, which is expressly incorporated herein by reference in its entirety.

FIELD OF THE DISCLOSURE

The present disclosure is directed to fluid treatment systems and methods. More particularly, the present disclosure relates to systems and methods for separating blood into its constituents and subsequently treating and/or collecting the constituents.

BACKGROUND

A variety of available blood processing systems allows for the collection and processing of particular blood components, rather than whole blood, from donors or patients. In the case of a blood donor, whole blood is drawn from the donor, a desired blood constituent separated and collected, and the remaining blood components returned to the donor. By removing only particular constituents rather than whole blood, it takes the donor's body a shorter time period to recover to normal blood levels, thereby increasing the frequency with which the donor may donate blood. It is beneficial to increase in this manner the overall supply of blood constituents made available for health care, such as red blood cells (RBCs), leukocytes, mononuclear cells (MNCs), plasma, and/or platelets, etc. In the case of a patient, whole blood is similarly drawn from the patient, a particular blood constituent first separated and then collected and/or treated, and the remaining blood components returned to the patient. The collected and/or treated blood constituent may be saved for future use, returned to the patient, and/or discarded and replaced with a suitable replacement.

The separation of blood components from whole blood typically takes place prior to the collection or treatment of the separated blood component and may be achieved through a spinning membrane or centrifugation, in which whole blood is passed through a centrifuge or membrane after it is withdrawn from the patient/donor. To avoid contamination and possible infection of the patient/donor, the blood is preferably contained within a sealed, sterile fluid flow system during the entire separation process. Typical blood processing systems thus may include a permanent, reusable hardware assembly containing the hardware (drive system, pumps, valve actuators, programmable controller, and the like) that pumps the blood, and a disposable, sealed and sterile fluid circuit that is mounted in cooperation on the hardware. In the case of separation via centrifugation, the hardware assembly includes a centrifuge that may engage and spin a separation chamber of the disposable fluid circuit during a blood separation step. The blood, however, may make actual contact only with the fluid circuit, which assembly may be used only once and then discarded or used for other purposes. In the case of separation via a spinning membrane, a disposable single-use spinning membrane may be used in cooperation with the hardware assembly and disposable fluid circuit.

In the case of separation via centrifugation, as the whole blood is spun by the centrifuge, the heavier (greater specific gravity) components, such as red blood cells, move radially outwardly away from the center of rotation toward the outer or "high-G" wall of the separation chamber of the fluid circuit. The lighter (lower specific gravity) components, such as plasma, migrate toward the inner or "low-G" wall of the separation chamber. Various ones of these components can be selectively removed from the whole blood by forming appropriately located channeling seals and outlet ports in the separation chamber of the fluid circuit.

In the case of separation via a spinning membrane, whole blood may be processed within a disposable spinning membrane, rather than within a separation chamber of a fluid circuit. Larger molecules, such as red blood cells, may be retained within one side of the membrane, while the smaller molecules, such as plasma, may escape through the pores of the membrane to the other side of the membrane. Various ones of these components can be selectively removed from the whole blood by forming appropriately located outlet ports in the housing of the membrane column. Various types of membranes with different pore sizes may be used, depending on the components to be separated.

In the case of MNC collection, which includes the collection of lymphocytes, monocytes, and/or stem cells, MNCs can be removed from the whole blood of a patient/donor, collected, and/or subjected to various therapies. Collected and treated MNCs may then be returned to the patient/donor for the treatment of various blood diseases by, e.g., eliminating immunogenicity in cells, inactivating or killing selected cells, inactivating viruses or bacteria, reconstituting the immune system, and/or activating desirable immune responses. MNC treatments are used for blood or solid organ/tissue cancers, photopheresis treatments, autologous and allogeneic stem cell transplants, donor lymphocyte infusions, research collections, etc.

SUMMARY

According to an exemplary embodiment, the present disclosure is directed to a method of collecting mononuclear cells, comprising separating whole blood into cellular components and platelet-rich plasma, separating the platelet-rich plasma into platelet concentrate and platelet-poor plasma, combining the cellular components with the platelet-poor plasma to form a first mixture, and separating the first mixture into mononuclear cells and at least one component.

According to an exemplary embodiment, the present disclosure is directed to an automated system of collecting mononuclear cells, comprising a disposable fluid circuit configured to work in association with a separator, the disposable fluid circuit comprising a plurality of fluid pathways and containers, wherein the separator is configured by a controller to separate whole blood into cellular components and platelet-rich plasma. The automated system also comprises a separation chamber forming a part of the disposable circuit, wherein a first compartment of the separation chamber is configured to receive the platelet-rich plasma and separate the platelet-rich plasma into platelet concentrate and platelet-poor plasma. The first compartment of the separation chamber is configured to direct the platelet-poor plasma to a second compartment of the separation chamber to combine with the cellular components to form a first mixture and separate the first mixture into mononuclear cells and at least one component.

According to an exemplary embodiment, the present disclosure is directed to a method of collecting mononuclear cells, comprising separating with a separator whole blood from a whole blood source into cellular components and platelet-rich plasma, returning the cellular components to the whole blood source, removing platelet-rich plasma to reduce platelet concentration of whole blood flowing into the separator, separating platelet-reduced whole blood from the whole blood source into cellular components and lower concentration platelet-rich plasma, and separating lower platelet concentration whole blood from the whole blood source into mononuclear cells and at least one component.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

DETAILED DESCRIPTION

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

Some embodiments may provide for collecting MNCs with reduced platelet interference during MNC harvest.

Some embodiments may provide for more accurate collection and harvest of MNCs by allowing for a clearer interface between blood component layers.

During harvest of MNCs, non-target substances may be present in the MNC product that can interfere with efficient harvesting of the target MNCs. For example, if a donor/patient has a high platelet count and/or other condition is present that alters platelet behavior and/or activation state, platelets may be induced to aggregate, clump, and/or build up within the separator, leading to challenges in proper and efficient MNC collection during leukapheresis. One mitigation practice has been to introduce more anticoagulant to the system, which may result in more anticoagulant being introduced into the patient/donor.

Some embodiments may be conducive to successful procedures being performed without excess anticoagulant being introduced to the system and/or patient/donor, thereby also leading to faster procedure times and higher collection efficiencies.

Figure 1:
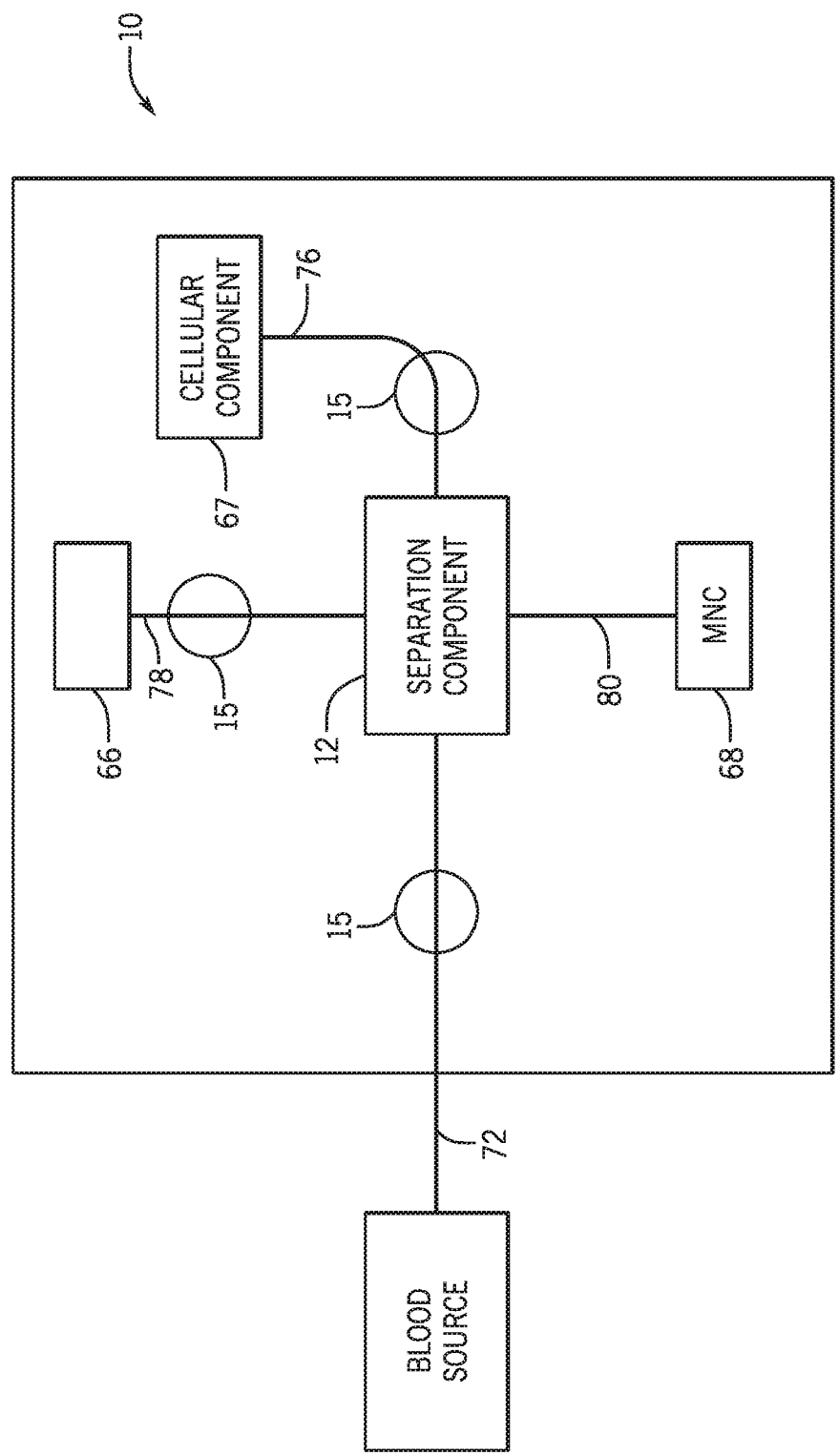
FIG. 1 is a diagrammatic depiction of a separation system useful in the separation and collection of mononuclear cells, according to an exemplary embodiment.
Figure 2:
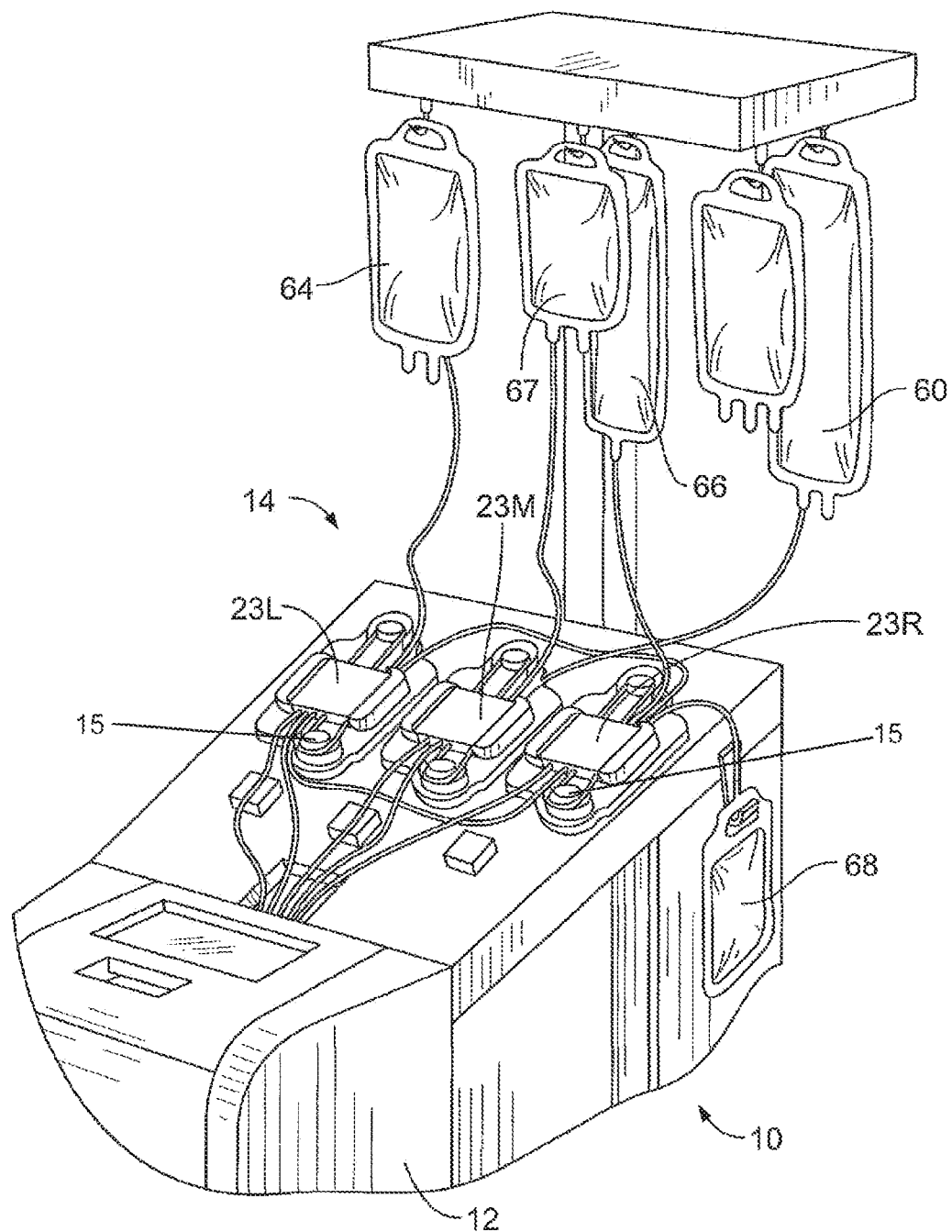
FIG. 2 is a perspective view of the front panel of a separation system with a disposable processing set for collecting mononuclear cells mounted on the device, according to an exemplary embodiment.

FIG. 1 is a diagrammatic depiction of a separation system 10 useful in the separation and collection of mononuclear cells, as described herein, and FIG. 2 shows an exemplary embodiment of the separation system 10. The system 10 may include a separation component 12 and a disposable processing kit 14 (FIG. 2) that is mounted thereon. Flow direction and rate may be controlled by a plurality of pumps 15 engaged with the processing kit 14. In one embodiment, the separation principle used by the separator 12 is based on centrifugation, but an automated separator based on a different separation principle (e.g., spinning membrane, etc.) may also be used.

A patient/donor may be connected to the fluid circuit 14, which may provide a sterile closed pathway between the separation component 12 and the remainder of the processing kit 14. Whole blood that is withdrawn from the patient/donor may be introduced into the separation component 12, where the whole blood may be separated to provide a target cell population, which in the context of the present disclosure may be mononuclear cells. Other components separated from the whole blood, such as red blood cells and platelets may be returned to the patient/donor or collected in pre-attached containers of the blood processing set. The separated target cell population, e.g., mononuclear cells, may then be collected for future use or prepared for various therapies.

Apparatus useful in the collection of mononuclear cells, and providing the separation component 12 of FIG. 1, include for example the Amicus® Separator made and sold by Fenwal, Inc., of Lake Zurich, Ill. Mononuclear cell collections using a device such as the Amicus® are described in greater detail in U.S. Pat. No. 6,027,657, the contents of which are incorporated by reference herein in its entirety. The fluid circuit 14 (FIG. 3) may include a blood processing container 16 defining a separation chamber suitable for harvesting MNCs from whole blood.

As shown in FIG. 2, a disposable processing set or fluid circuit 14 (which includes container 16) may be mounted on the front panel of the separation component 12. The processing set (fluid circuit 14) may include a plurality of processing fluid flow cassettes 23L, 23M and 23R with tubing loops for association with peristaltic pumps 15 on the separation component 12. Fluid circuit 14 may also include a network of tubing and pre-connected containers for establishing flow communication with the patient/donor and for processing and collecting fluids and blood and blood components, as shown in greater detail in FIG. 3.

Figure 3:
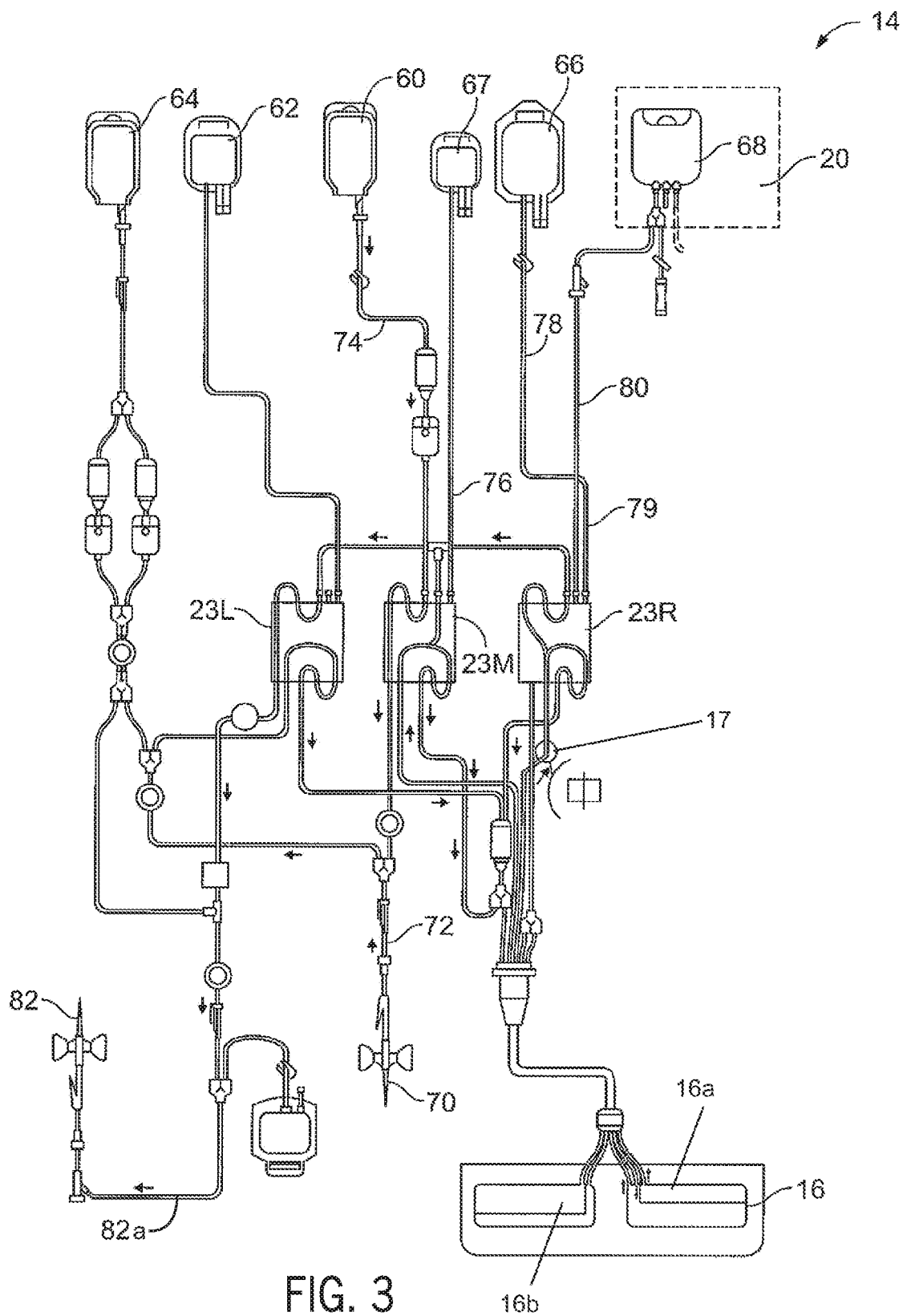
FIG. 3 is a diagram showing the disposable processing set of FIG. 2, according to an exemplary embodiment.

As seen in FIG. 3, the disposable processing set 14 may include a container 60 for supplying anticoagulant, an in-process container 62, a container 64 for holding a crystalloid solution, such as saline, a container 66 for collecting plasma, and a container 68 for collecting the mononuclear cells.

With reference to FIG. 3, fluid circuit 14 may include inlet line 72, an anticoagulant (AC) line 74 for delivering AC from container 60, an RBC line 76 for conveying red blood cells from chamber 16 of set 14 to container 67, a plasma line 78 for conveying plasma to container 66 and line 80 for conveying mononuclear cells to and from separation chamber 16 and collection container 68.

The blood processing set may also include one or more venipuncture needle(s) or access device(s) for accessing the circulatory system of the patient/donor. As shown in FIG. 3, fluid circuit 14 may include inlet access device 70 and return access device 82. In an alternative embodiment, a single access device may serve as both the inlet and outlet access device.

Fluid flow through fluid circuit 14 may be driven, controlled and adjusted by a microprocessor-based controller in cooperation with the valves, pumps, weight scales and sensors of separation component 12 and fluid circuit 14, the details of which are described in the previously mentioned U.S. Pat. No. 6,027,657.

A separation chamber may be defined by the walls of the processing container 16. The processing container 16 may comprise two different compartments 16a and 16b (FIG. 3). Using both compartments 16a and 16b for separation in a procedure may enable multiple target products to be separated simultaneously and/or multiple steps to be completed simultaneously. If only one compartment is used for separation, the other compartment may optionally be used as an in-process, waste, or storage container. In operation, the separation device 12 may rotate the processing container 16 about an axis, creating a centrifugal field within the processing container 16. Details of the mechanism for rotating the processing container 16 are disclosed in U.S. Pat. No. 5,360,542 titled "Centrifuge with Separable Bowl and Spool Elements Providing Access to the Separation Chamber," which is also incorporated herein by reference in its entirety.

In one embodiment, an apheresis device or system 10 may include a programmable controller that is pre-programmed with one or more selectable protocols. A user/operator may select a particular processing protocol to achieve a desired outcome or objective. The pre-programmed selectable protocol(s) may be based on one or more fixed and/or adjustable parameters. During a particular processing procedure, the pre-programmed controller may operate the separator 12 and processing chamber 16 associated therewith to separate blood into its various components, as well as operate one or more pumps to move blood, blood components and/or solutions through the various openable valves and tubing segments of a processing set, such as processing set 14 illustrated in FIG. 3. The various processing steps performed by the pre-programmed automated apheresis device may occur separately, in series, simultaneously or any combination of these.

An automated apheresis device may be used to perform MNC collection in a batch process in which MNCs continuously collect in the chamber 16 until the target cycle volume is reached. During the continuous collection of MNCs within the chamber 16, different blood components separate into layers that may be detected by an optical interface detector that monitors the location and presence of the interface between layers. Details of an exemplary mechanism for interface detection are disclosed in U.S. Pat. No. 6,027,657, the contents of which are incorporated by reference herein in its entirety. Before and during the transfer of the MNCs out of the chamber 16, MNCs and other blood components (e.g., plasma, platelets, etc.) may pass through an optical sensor 17, located downstream of the chamber 16, which detects the presence of cells in the tubing line to determine the start and end of the MNC harvest (i.e. when to open and close the valves leading to the product container). The term "downstream" describes an event proximal to post-separation, and the term "upstream" describes an event proximal to pre-separation. "Downstream" and "upstream" are relative terms, with the reference point being the time/location of separation. After MNC harvest is complete, the remaining cells in the line may be flushed into the product container with a predetermined volume of plasma known as the "plasma flush".

The ability of the separation chamber to efficiently harvest the MNCs may be facilitated by removal of non-target substances (e.g., platelets) that may be present in the blood that can interfere with the separation procedure. Additionally, the removal of non-target substances may improve the ability of the optical sensor 17 to accurately detect the presence of cells in the tubing line to determine the start and end of the MNC harvest to facilitate precise harvesting of the target MNCs.

EXAMPLES

Figure 4A:
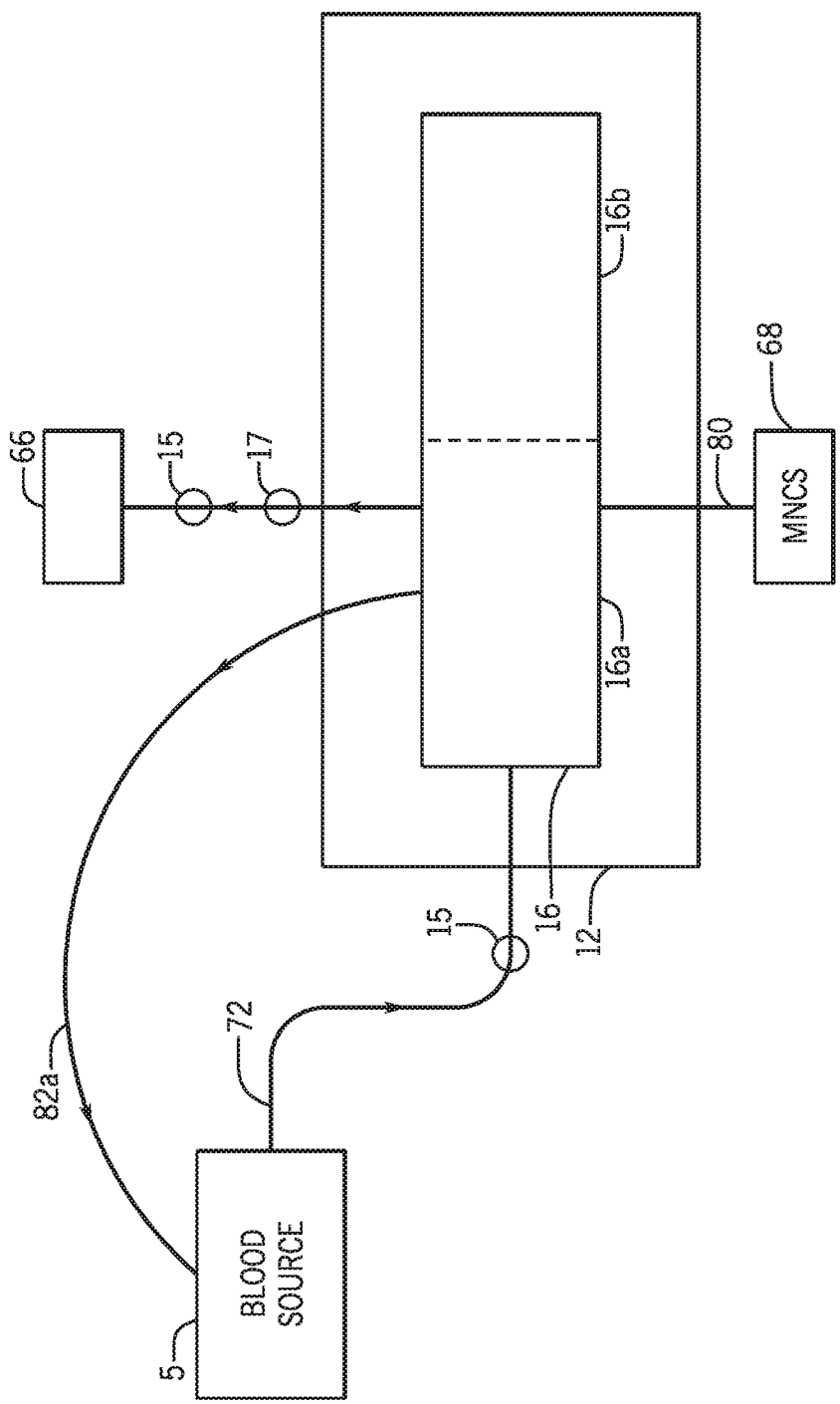
FIGS. 4A-4C are diagrammatic depictions illustrating a method for obtaining mononuclear cells, according to several exemplary embodiments.

Without limiting any of the foregoing, the subject matter described herein may be found in one or more methods, systems and/or products. For example, in one aspect of the present subject matter, an improved system and method for obtaining MNCs is set forth in FIG. 4A. The inlet access device 70 of FIG. 3 attached to inlet line 72 may first be connected to a blood source 5 (e.g., donor, patient, blood bag, etc.). Whole blood may enter the separation chamber 16 of the separator 12, which separates the whole blood into cellular components and platelets suspended in plasma. FIG. 4A shows the separation into cellular components and platelets suspended in plasma taking place in compartment 16a, but either compartment 16a or 16b may be used. The platelets and plasma (referred to as "platelet-rich plasma") may be separated and directed into container 66, and the cellular components may be separated and returned to the patient/donor via return line 82a and access device 82 (FIG. 3). An optical sensor 17 may be placed downstream of the separation chamber 16a or 16b at a tubing line leading to container 66 to determine when a sufficient amount of platelets has been removed and platelet-rich plasma is clear enough for the removal of platelets suspended in plasma into container 66 to stop.

Once a sufficient amount of non-target content (e.g., platelets) has been removed into container 66, MNC collection may begin. Referring to FIG. 4A, whole blood from the blood source 5 (e.g., donor, patient, blood container, etc.) may enter the separation chamber 16 of the separator 12 into either compartment 16a or 16b via the inlet needle access device 70 (FIG. 3) attached to inlet line 72. Within the separation chamber 16, the separator 12 may separate the whole blood into lower concentration platelet-rich plasma (due to some of the platelets having been removed earlier into container 66), MNCs, and remaining cellular components (e.g., RBCs). While MNCs continuously collect within the chamber 16, the lower concentration platelet-rich plasma and remaining cellular components may be separated and directed back to the blood source 5 via return line 82a and/or stored for later use. Upon the target amount of MNCs having been collected and remaining cellular components and lower concentration platelet-rich plasma having been returned to the blood source 5 and/or stored, the collected MNCs may be harvested into a designated container 68 to be processed for further treatment, and the platelets suspended in plasma in container 66 used for other purposes or discarded.

Figure 4B:
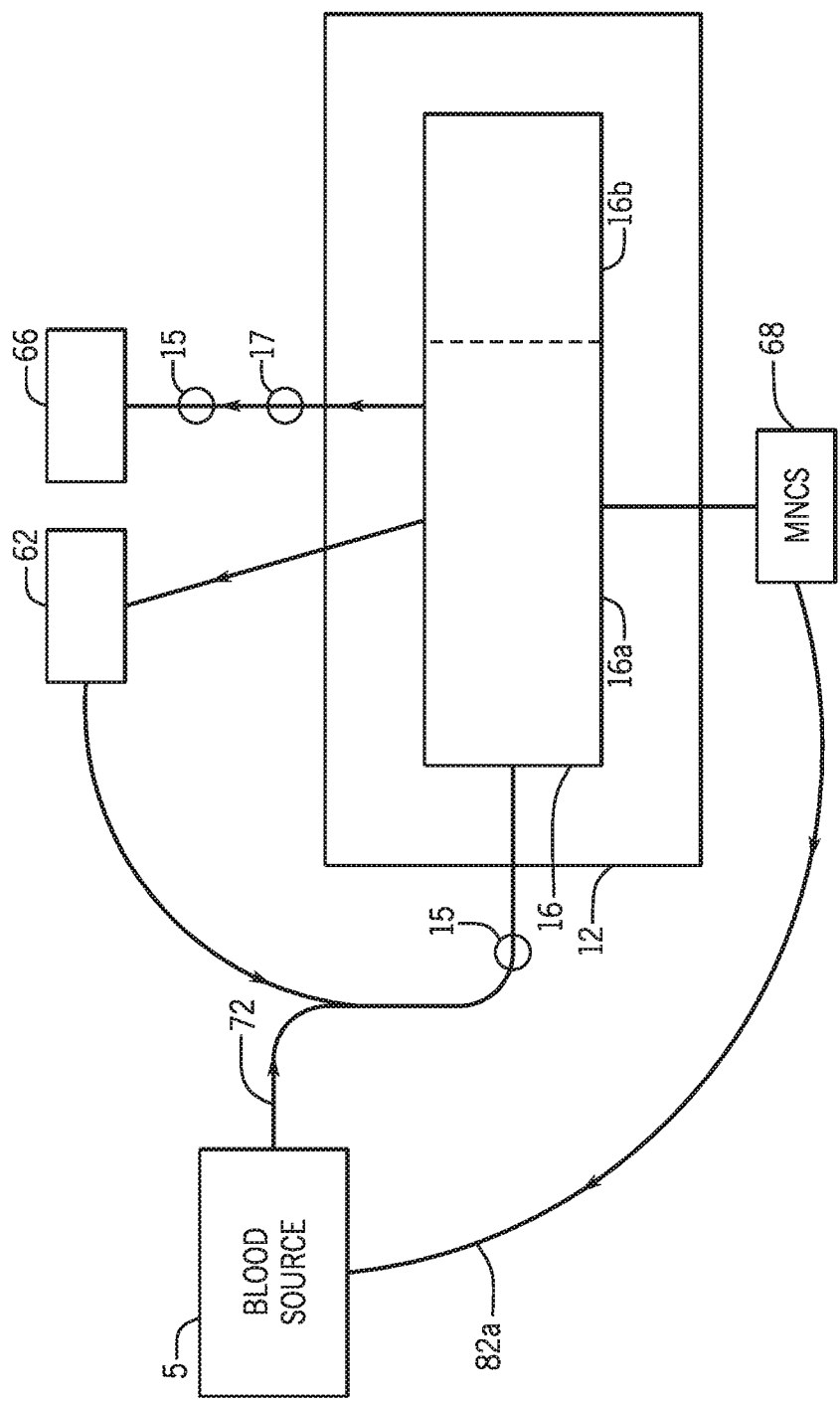

In another aspect of the present subject matter, an improved system and method for obtaining MNCs is set forth in FIG. 4B. The inlet line 72 may be connected to a blood source 5 (e.g., donor, patient, blood bag, etc.). Whole blood may enter the separation chamber 16 of the separator 12, which separates the whole blood into cellular components and platelet-rich plasma. FIG. 4B shows the separation into cellular components and platelet-rich plasma taking place in compartment 16a, but either compartment 16a or 16b may be used. The platelet-rich plasma may be separated and directed into in-process container 62, and the cellular components may be separated and returned to the patient/donor via return line 82a. When all cellular components have left the separation chamber 16, the platelet-rich plasma in in-process container 62 may be directed back into the separation chamber 16 (into either compartment 16a or 16b) to be separated into plasma and platelet concentrate. The platelet concentrate may be directed to container 66 or another container to be discarded or used for other purposes, and the separated plasma may be returned to the blood source 5 via return line 82a and/or stored for later use.

Once a sufficient amount of non-target content (e.g., platelets) has been removed into container 66, MNC collection may begin. Referring to FIG. 4B, whole blood from the blood source 5 (e.g., donor, patient, blood bag, etc.) may enter the separation chamber 16 of the separator 12 into either compartment 16a or 16b via the inlet line 72. Within the separation chamber 16, the separator 12 may separate the whole blood into lower concentration platelet-rich plasma (due to some of the platelets having been removed earlier into container 66), MNCs, and remaining cellular components (e.g., RBCs). While MNCs continuously collect within the chamber 16, the lower concentration platelet-rich plasma and remaining cellular components may be separated and directed back to the blood source 5 via return line 82a and/or stored for later use. Upon the target amount of MNCs having been collected and remaining cellular components and lower concentration platelet-rich plasma having been returned to the blood source 5 and/or stored, the collected MNCs may be harvested into a designated container 68 to be processed for further treatment.

Figure 4C:
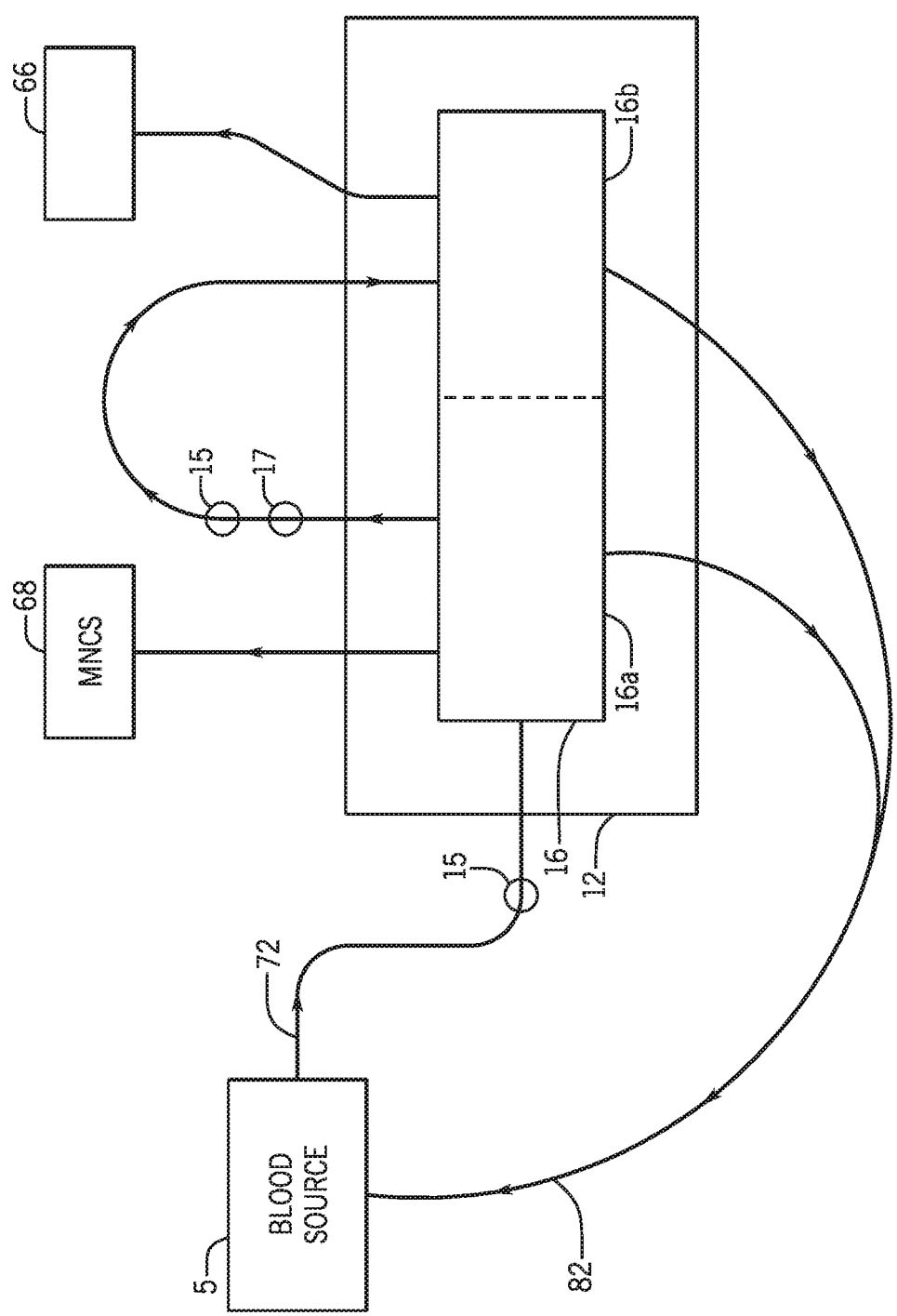

The process and steps of whole blood initially being separated into cellular components and platelet-rich plasma and the platelet-rich plasma being separated into platelet concentrate and plasma portrayed in FIG. 4B may take place substantially in series if only one compartment 16a or 16b is utilized. In another aspect of the present subject matter, a system and method for obtaining MNCs is set forth in FIG. 4C, in which the process and steps of whole blood initially being separated into cellular components and platelet-rich plasma and the platelet-rich plasma being separated into platelet concentrate and plasma may take place substantially at the same time when both compartments 16a and 16b are utilized. Turning to FIG. 4C, the inlet line 72 may be connected to a blood source 5 (e.g., donor, patient, blood bag, etc.). Whole blood may enter the separation chamber 16 of the separator 12 at a first compartment, e.g., compartment 16a, where whole blood may be separated into cellular components and platelet-rich plasma. The platelet-rich plasma may be directed into a second compartment, e.g., compartment 16b, of the separation chamber 16, and the cellular components may be separated and returned to the blood source 5 via return line 82a. Substantially at the same time that the whole blood is being separated in compartment 16a into cellular components and platelet-rich plasma, the platelet-rich plasma directed to compartment 16b may be separated into plasma and platelet concentrate within compartment 16b. The separated plasma may be returned to the blood source 5 via return line 82a and/or stored for later use. The platelet concentrate may be directed to container 66 or another container to be discarded or used for other purposes, or may remain within compartment 16b. An optical sensor 17 may be placed downstream of the first compartment 16a to determine when a sufficient amount of platelets has been removed and platelet-rich plasma is clear enough for the separation of plasma and platelet concentrate in the second compartment 16b to stop.

Once a sufficient amount of non-target content (e.g., platelets) has been removed and/or interference with separation is minimized, MNC collection may begin. Referring to FIG. 4C, whole blood from the blood source 5 (e.g., donor, patient, blood bag, etc.) may enter the separation chamber 16 of the separator 12 into either compartment 16a or 16b via the inlet line 72. If the platelet concentrate has been left to recirculate and remain within a compartment in the previous step, the whole blood may be directed to the compartment that does not contain the platelet concentrate, e.g., compartment 16a. Within compartment 16a of separation chamber 16, the separator 12 may separate the whole blood into lower concentration platelet-rich plasma (due to some of the platelets having been removed earlier in compartment 16b), MNCs, and remaining cellular components (e.g., RBCs). While MNCs continuously collect within compartment 16a of separation chamber 16, the lower concentration platelet-rich plasma and remaining cellular components may be separated and directed back to the blood source 5 via return line 82a and/or stored for later use. Upon the target amount of MNCs having been collected and remaining cellular components and lower concentration platelet-rich plasma having been returned to the blood source 5 and/or stored, the collected MNCs may be harvested into a designated container 68 to be processed for further treatment.

Figure 5:
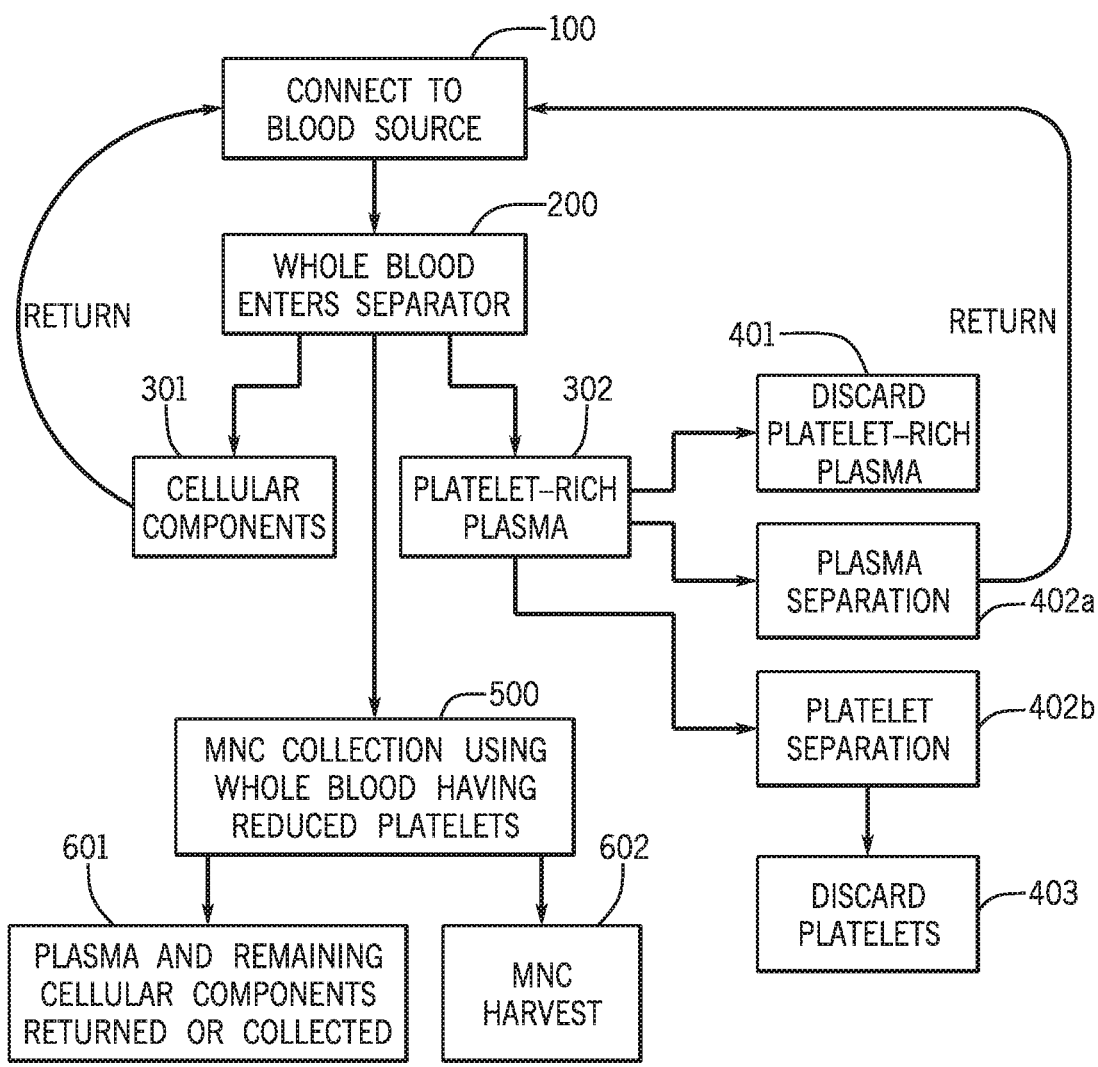
FIG. 5 is a flow diagram illustrating a method for obtaining mononuclear cells, according to an exemplary embodiment.

In another aspect of the present subject matter, a method for obtaining MNCs is set forth in FIG. 5. An inlet access device or connector may first be connected to a blood source 5 (e.g., donor, patient, blood bag, etc.) at step 100 of FIG. 5. At step 200, whole blood enters a separator, which separates the whole blood into cellular components (step 301) and platelet-rich plasma (step 302). In the embodiment in FIG. 5, the separator of step 200 may be a centrifugal or spinning membrane separator. An exemplary spinning membrane and hardware is disclosed in greater detail in PCT Patent Application No. PCT/US2012/28492, which is incorporated herein by reference in its entirety, although any suitable membrane assembly may be used. Cellular components separated at step 301 may be returned to the blood source 5. Platelet-rich plasma separated at step 302 may be discarded or used for other purposes at step 401 or be further separated into platelet concentrate (step 402b) and plasma (step 402a). The platelet concentrate may be discarded or used for other purposes (step 403), and the plasma may return to the blood source 5.

At step 500, when an adequate amount of non-target content (e.g., platelets) has been removed and/or interference with separation is minimized, MNC collection may begin. The separator may separate whole blood having reduced platelets into plasma, MNCs and remaining cellular components. The MNCs may be harvested at the end of the procedure at step 602, and the plasma and remaining cellular components may be returned to the blood source or collected at step 601.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. A method of collecting mononuclear cells, comprising:
   separating with a separator whole blood from a whole blood source into cellular components and platelet-rich plasma;
   removing the cellular blood components and the platelet-rich plasma from the separator;
   returning the cellular components to the whole blood source without returning at least a portion of the platelets in the platelet-rich plasma to the whole blood source to reduce platelet concentration of whole blood subsequently flowing into the separator from the whole blood source; and
   separating lower platelet concentration whole blood from the whole blood source into mononuclear cells and at least one component.

2. The method of claim 1, further comprising stopping the separation of whole blood from the whole blood source into cellular components and platelet-rich plasma when an optical sensor disposed downstream of the separator detects that the platelet-rich plasma removed from the separator has a target platelet concentration.

3. The method of claim 1, wherein the separator comprises a spinning membrane separator.

4. The method of claim 1, wherein the separator comprises a centrifugal separator.

5. The method of claim 1, wherein said separating whole blood into cellular components and platelet-rich, plasma and said separating lower platelet concentration whole blood into mononuclear cells and at least one component are performed substantially in series.

6. The method of claim 1, wherein said separating lower platelet concentration whole blood from the whole blood source into mononuclear cells and at least one component includes separating the lower platelet concentration whole blood into mononuclear cells, a primarily plasma component, and remaining cellular components.

7. The method of claim 1, further comprising
   returning the platelet-rich plasma to the separator,
   separating the platelet-rich plasma in the separator into platelet-poor plasma and platelet concentrate, and
   removing the platelet-poor plasma from the separator.

8. The method of claim 7, further comprising returning the platelet-poor plasma to the whole blood source without returning the platelet concentrate to the whole blood source.

9. The method of claim 7, wherein said separating whole blood into cellular components and platelet-rich plasma and said separating the platelet-rich plasma into platelet-poor plasma and platelet concentrate are performed substantially in series.

10. The method of claim 7, wherein said separating whole blood into cellular components and platelet-rich plasma and said separating the platelet-rich plasma into platelet-poor plasma and platelet concentrate are performed substantially at the same time.

11. A blood separation system, comprising:
    a separator including a controller; and
    a disposable fluid circuit configured to work in association with the separator, wherein the controller is configured to control the separator to
    separate whole blood from a whole blood source into cellular components and platelet-rich plasma,
    remove the cellular blood components and the platelet-rich plasma from the separator,
    return the cellular blood components to the whole blood source without returning at least a portion of the platelets in the platelet-rich plasma to the whole blood source to reduce platelet concentration of whole blood subsequently flowing into the separator from the whole blood source, and
    separate lower platelet concentration whole blood from the whole blood source into mononuclear cells and at least one component.

12. The blood separation system of claim 11, further comprising an optical sensor disposed downstream of the separator, wherein the controller is configured to stop separation of whole blood from the whole blood source into cellular components and platelet-rich plasma when the optical sensor detects that the platelet-rich plasma removed from the separator has a target platelet concentration.

13. The blood separation system of claim 11, wherein the separator comprises a spinning membrane separator.

14. The blood separation system of claim 11, wherein the separator comprises a centrifugal separator.

15. The blood separation system of claim 11, wherein the controller is configured to control the separator to separate whole blood into cellular component and platelet-rich plasma and to separate lower platelet concentration whole blood into mononuclear cells and at least one component substantially in series.

16. The blood separation system of claim 11, wherein the controller is configured to control the separator to separate lower platelet concentration whole blood from the whole blood source into mononuclear cells and at least one component by separating the lower platelet concentration whole blood into mononuclear cells, a primarily plasma component, and remaining cellular components.

17. The blood separation system of claim 11, wherein the controller is configured to control the separator to
    return the platelet-rich plasma to the separator,
    separate the platelet-rich plasma in the separator into platelet-poor plasma and platelet concentrate, and
    remove the platelet-poor plasma from the separator.

18. The blood separation system of claim 17, wherein the controller is configured to control the separator to return the platelet-poor plasma to the whole blood source without returning the platelet concentrate to the whole blood source.

19. The blood separation system of claim 17, wherein the controller is configured to control the separator to separate whole blood into cellular components and platelet-rich plasma and to separate the platelet-rich plasma into platelet-poor plasma and platelet concentrate substantially in series.

20. The blood separation system of claim 17, wherein the controller is configured to control the separator to separate whole blood into cellular components and platelet-rich plasma and to separate the platelet-rich plasma into platelet-poor plasma and platelet concentrate substantially at the same time.

* * * * *